United States Patent [19]

Gregory

[11] Patent Number: 4,592,823
[45] Date of Patent: Jun. 3, 1986

[54] FLUSHABLE REFERENCE CELL FOR POTENTIOMETRIC MEASUREMENTS

[75] Inventor: Walter J. Gregory, Newtown, Pa.

[73] Assignee: Rohm and Haas Company, Philadelphia, Pa.

[21] Appl. No.: 765,745

[22] Filed: Aug. 15, 1985

[51] Int. Cl.$^4$ .............................................. G01N 27/30
[52] U.S. Cl. ................................... 204/409; 204/402; 204/435; 324/425; 324/438
[58] Field of Search ................. 204/435, 402, 409; 324/425, 438

[56] References Cited

U.S. PATENT DOCUMENTS

| | | | |
|---|---|---|---|
| 3,486,997 | 12/1966 | Petersen | 204/435 |
| 3,997,420 | 12/1976 | Buzza | 204/411 |
| 4,282,081 | 8/1981 | Arrance, Sr. | 204/435 |
| 4,285,792 | 8/1981 | McGandy | 204/402 |
| 4,378,280 | 3/1983 | Dufau | 204/435 |
| 4,390,406 | 6/1983 | Kato et al. | 204/435 |
| 4,401,548 | 8/1983 | Brezinski | 204/435 |

Primary Examiner—G. L. Kaplan

[57] ABSTRACT

The clogging of junctions of electrochemical reference cells by contaminants is prevented by a triple junction design incorporating dual, independently operative flushing conduits. The first conduit flushes the exterior of the first junction and the exterior of the second junction, and the second conduit flushes the interior of the second junction and the exterior of the third junction. When the cell is used in-line on a chemical process stream, pressure equalizing means are employed between the stream and the standard electrode, of which the third junction is an element. Elevation of the exits of the flushing conduits above the junctions releases air from the cell which may collect at the junctions and impair the accuracy of the readings.

9 Claims, 1 Drawing Figure

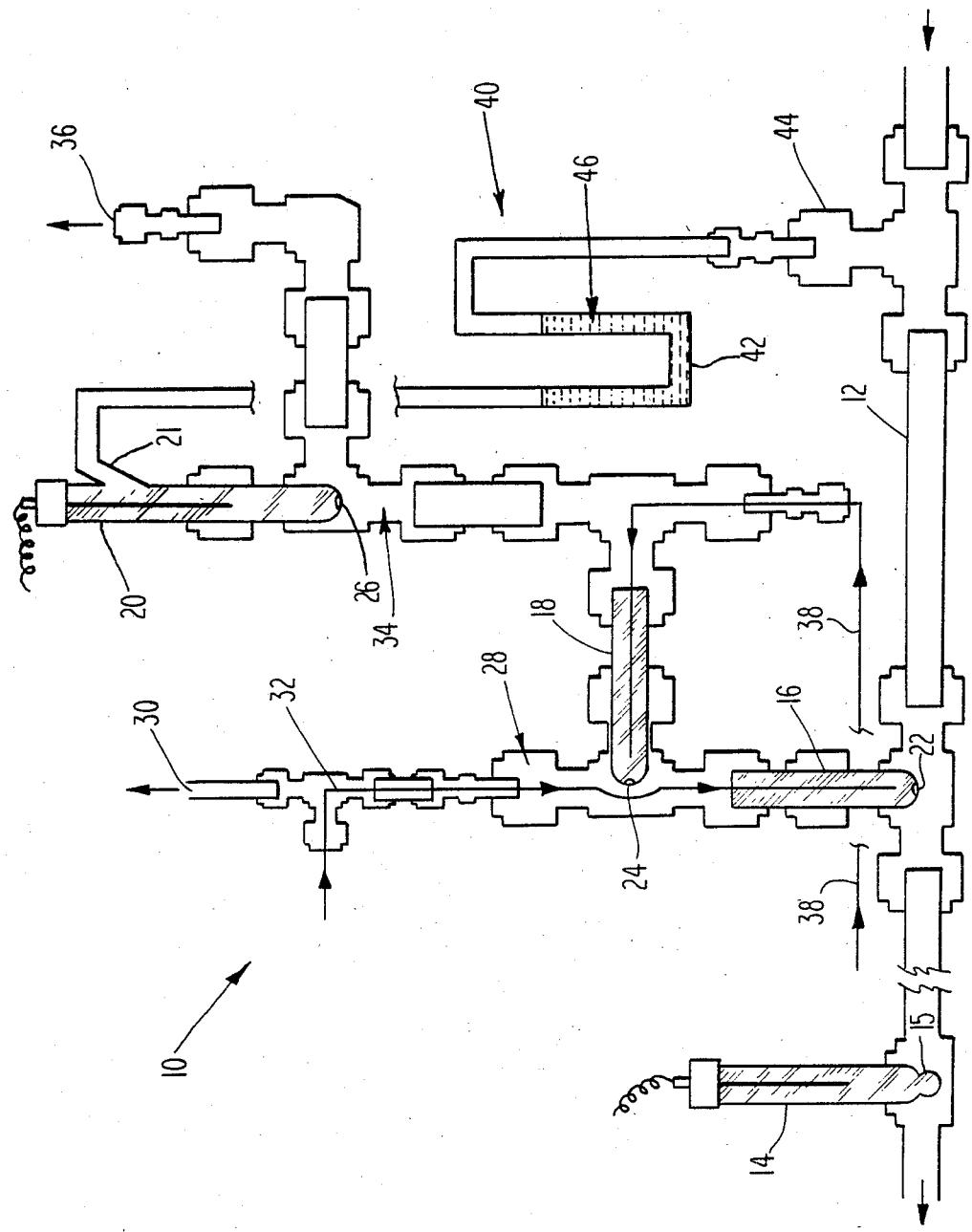

FLUSHABLE REFERENCE CELL FOR POTENTIOMETRIC MEASUREMENTS

BACKGROUND OF THE INVENTION

This invention relates to ion sensitive electrodes, and more particularly to electrochemical reference cells incorporating flushing means for removing contaminants or clogging material from the cells.

In many chemical processes, it is important to monitor or control the concentrations of selected ionic species in order to influence reaction by adjusting the concentrations thereof or modifying other reaction conditions. Typical of such measurements is the potentiometric determination of hydrogen ion concentration with pH probes incorporating a measuring cell and a reference cell. A common problem of electrochemical pH measurement or electrochemical determination of other ionic species is reaction, in the reference cell, between the heavy metal salts used as reference electrodes, such as silver chloride or mercury chloride, with certain ionic species present or generated in the aqueous medium in contact with the reference cell, such as reactants, by-products or impurities, soluble or insoluble, collectively hereinafter sometimes called "contaminants". Characteristically, a contaminant diffuses across an electrochemical junction (such as a porous, ion permeable member including ceramic plugs, membranes and fibrous materials) into the electrolyte solution of a cell and is carried by the electrolyte to the reference electrode where it reacts with the heavy metal salts. The resulting reaction products usually are insoluble and (together with the contaminant itself, if insoluble) collect at the junction. As the junction becomes clogged with the insoluble material, an erroneous potential is generated across the junction due to restriction of ion transport through the junction. Eventually the insoluble material will clog the junction and entirely prevent hydrogen ion determination or measurement of other ionic species.

In attempts to remedy the foregoing problem, double junction reference cells of many different designs have been developed, as illustrated by U.S. Pat. Nos. 4,282,081, 4,390,406 and 4,401,548. In these cells, a second porous junction is combined with the porous junction of the conventional reference electrode with the zone between the junctions filled with an electrolytic liquid such as a potassium chloride solution. Although this design reduces the rate of reference cell failures when the reference cells have only intermittent or brief exposures to a sample containing a contaminant, the failure rate greatly increases and becomes unacceptable when the reference cells are to be used for continuous, in-line measurements.

In another approach to alleviating the junction-clogging problem, reference cells have been designed with cleansing or flushing systems, frequently in combination with double junctions. U.S. Pat. Nos. 3,486,997, 3,997,420, 4,285,792 and 4,378,280 are representative of reference cells incorporating flushing means. Nevertheless, such cells remain unsatisfactory for various reasons, including requirements for awkward mechanical elements such as valves and pumps, limitation to flushing of only portions of the reference cells and inapplicability to continuous, long-term exposure to contaminants in a sample, (both quiescent liquids and mobile chemical process streams), wherein it is desired that the exposure will require only minimal care from plant personnel.

SUMMARY OF THE INVENTION

It has now been found that build-up and eventual clogging of junctions in electrochemical reference cells intended for long-term exposure to sample liquids which contain or generate contaminants, can be eliminated or minimized by a reference cell characterized by three junctions and dual, independently operative flushing systems, which flushing systems can be remotely and automatically regulated.

Briefly, in one aspect of the invention, a reference cell is provided which comprises, in combination, a first tubular, standard electrolyte-containing compartment having an ion-permeable member defining a first junction for contact with a sample solution; a second tubular, standard electrolyte-containing compartment having an ion-permeable member defining a second junction for contact with the standard electrolyte contained in the first tubular compartment; a third tubular, standard electrolyte- and electrode-containing compartment having an ion-permeable member defining a third junction for contact with the standard electrolyte contained in the second tubular compartment, the third tubular compartment including a conductor for electrical contact between the electrode and a potentiometer; first fluid-conducting means between the first tubular compartment and the exterior of the second tubular compartment; second fluid-conducting means between the interior of the second tubular compartment and the exterior of the third tubular compartment; a first fluid conduit positioned to deliver a first flushing liquid to the first junction interiorly of the first tubular compartment, and to the second junction exteriorly of the second tubular compartment; first exit means for removal of the first flushing liquid; a second fluid conduit positioned to deliver a second flushing liquid to the second junction interiorly of the second tubular compartment, and to the third junction exteriorly of the third tubular compartment; and second exit means for removal of the second flushing liquid.

In another aspect of the invention, the elevations of the exit means relative to the junctions are such as to prevent or minimize the collection of air around the junctions, such air sometimes being a cause of erroneous readings.

In a further aspect of the invention, the flushing liquids include a reagent which reacts with potential clogging material, thereby facilitating removal in a flushing sequence.

In still another aspect of the invention, having applicability to measurement of ionic species in a moving stream, fluid pressure equalizing means are incorporated into the reference cell to offset or prevent passage of contaminants through the junctions which eventually may cause the junctions to clog.

BRIEF DESCRIPTION OF THE DRAWING

The single FIGURE shows a typical embodiment of a triple-junction apparatus of the invention.

DETAILED DESCRIPTION

An embodiment of the invention is illustrated schematically in the drawing. With reference thereto, a flushable reference cell 10 of the invention is shown in a mode for potentiometric analysis of a liquid stream, such as a chemical process liquid, in a conduit 12. A conventional measuring electrode 14 having an ion impermeable junction 15, such as a thin glass membrane, is mounted in a sector of conduit 12 and is electrically connected to a potentiometer (not shown). (It will be apparent that junction 15 may be replaced with an ion permeable material if the measuring electrode is to be used for electrochemical measurement of ionic species other than hydrogen ion.) The reference cell 10 produces a constant potential, independent of hydrogen ion concentration, by means of a standard electrode comprising a conductor in contact with a paste of a heavy metal and a salt of the metal, such as silver/silver chloride or mercury/mercury chloride ("calomel"). The reference cell 10 accordingly comprises glass tubes 16 and 18 and a standard half-cell electrode tube 20 each containing an aqueous salt solution. Tube 20 also contains an electrolytic paste (such as the silver/silver chloride or mercury/mercury chloride mixtures already mentioned) in contact with a conductor and the electrolytic salt solution. The conductor is electrically connected through a suitable lead to the potentiometer (not shown) to which is also connected measuring cell 14. Tube 20 optionally may be fitted with a side-arm 21 for connection to other tubing for purposes described below.

Tubes 16, 18 and 20 have small openings (about 1 mm.) in their tips plugged with an electrolytic solution-permeable material (such as filter paper, a ceramic filter or a porous membrane) to form porous junctions 22, 24 and 26, respectively, for ionic transport. The opposing ends of tubes 16 and 18 are open. The opposing end of tube 20 is sealed except for an optional opening for electrolyte refill (not shown) and the opening to side arm 21. The open end of tube 16 is sealingly engaged by suitable fittings with a conduit 28 having an exit 30.

An entry conduit such as tube 32 is sealingly mounted within conduit 28 with its lower, open end in proximity to junction 22. Tube 32 is adapted for transport of a flushing liquid to the proximity of junction 22 (interiorly of tube 16) and junction 24 (exteriorly of tube 18). The flushing liquid may be any electrolyte solution which is compatible with the components of the cell. Salt solutions such as 4 M KCl solution are suitable. The flushing liquid admitted by tube 32 exits via conduit 28 at 30. Conduit 28 also operates as an isolation bridge to minimize diffusion through junction 24 of contaminant which may enter tube 16 through junction 22 from conduit 12. Liquid admitted by tube 32 serves to react with and/or flush away from junctions 22 and 24 and then to remove through exit 30, any contaminant or insoluble reaction product which may have built up at junctions 22 and 24. As described above, these contaminants, if not removed in a timely fashion, will clog the junctions and result in generation of an erroneous potential across the junctions due to a restriction of ion transport through the junctions. Eventually, the junctions will become so clogged as to make potentiometric measurement impossible. The combination of conduit 28, tube 32 and flushing liquid thus operates as a first flushing system to maintain one side of reference cell 10 free of contamination.

The reference cell 10 further includes a second flushing system of which conduit 34 is one element. Conduit 34 sealingly engages glass tubes 18 and 20 and has an exit 36 for flushing liquid admitted by the second element of the flushing system, an entry conduit such as tube 38. Tube 38 opens in the vicinity of junction 24, interiorly of tube 18, so as to react with and/or flush away from junction 24 any contaminant or reaction product which may have there collected. Should contaminant (or reaction product of a contaminant) have diffused through junction 24 into tube 18, conduit 34 acts as a protection bridge by bringing into contact with the contaminant or reaction product, via tube 38, a flushing liquid which will react with or/and dislodge the contaminant or reaction product and cause it to be removed from junctions 24 and 26 via exit 36. The flushing liquid can be the same electrolyte as the flushing liquid of the first flushing system but preferably will be the same solution used in standard electrode tube 20, since this solution contains a component, such as a silver salt, which will react with and thereby remove, contaminants such as sulfides.

Although the drawing shows flushing liquid conduits 32 and 38 as positioned generally concentric in conduits 38 and 34, and having entry and exit ports positioned to maximize fluid pressure at the three junctions while providing for efficient flushing of contaminants and insoluble materials from the cell, conduit 32 and/or conduit 38 may be positioned otherwise. For example, the conduits could enter conduits 28 and 34 in the vicinity of the upper, open ends of tubes 16 and 18 or could be mounted in the walls of tubes 16 and 18 in proximity to junctions 22 and 24. Similarly, conduit 38 may be branched so as to cause impingement of flushing liquid directly onto junction 26, or one or more other conduits for flushing liquid can be added to the system to further enhance the flushing action.

As described to this point, the reference cell 10 is effective for potentiometric analysis of quiescent liquids in conduit 12. However, if the liquid in conduit 12 is a moving stream, fluid pressure imposed on the junctions 22, 24 and 26 must be equalized by a pressure equalizer system 40. In one embodiment of such system, there is shown in the drawing a U-tube 42 connected at its lower end to conduit 10 via a fitting 44 and at its upper end to standard electrode tube 20 via side arm 21. The U-tube contains a material 46 (such as a concentrated electrolyte, an electrolytic paste or salt crystals) having the same composition as the electrolytic paste in tube 20. Typically, material 46 is a silver chloride or mercury chloride paste. By virtue of the liquid equalizing pressure provided by system 40, bulk flow of liquid from conduit 12 through junctions 22, 24 and 26 is prevented. Material 46 also reacts with contaminants in conduit 12 that may enter tube 20 from U-tube 42.

Other pressure equalizing means may be used in place of the U-tube embodiment 40, such as a conventional pneumatic pressure regulator based upon pressure equalization with an inert gas such as nitrogen.

Flushing liquids normally will be delivered via tubes 32 and 38 periodically, depending upon experience with the reference cell in potentiometric analysis. Such experience involves, as previously described, the possibility of diffusion of contaminants from conduit 12 through junctions 22 and 24 and clogging of these junctions as well as junction 26. The two flushing systems can be operated simultaneously or sequentially as experience dictates. Normally, when a potentiometric analysis is underway and readings from measuring cell 14 are being recorded, the flushing systems will not be operated.

The fittings for the various components of the reference cell 10 will be selected from the standpoint of inertness—to the various liquids and dimensional stability at operating temperature. For example, nylon fittings in conjunction with glass electrode tubes and conduits are preferred over other materials, such as stainless steel. However, Teflon plastic may also be employed for the conduits.

In a preferred arrangement of the reference cell 10, as shown in the drawing, exit 30 to conduit 28 is positioned above junctions 22 and 24, and exit 36 to conduit 34 is positioned above junction 26. It has been found that these relative positions prevent collection of air, if any should enter the system, around junctions 24 and 26, because the air will pass out of the system from exits 30 and 36 by virtue of the relatively higher elevations of the exits. If the air should collect at junctions 24 and/or 26, as bubbles or foam for example, ion transport through the junctions will be impeded, thereby interrupting the circuit and preventing accurate readings.

It will be obvious that operation of the reference cell of the invention can be automated and computer controlled in conjunction with chemical processing of which the cell may form a part. Also, since the accuracy of potentiometric analysis is temperature related, the reference cell or the measuring cell, or both, may be operated under controlled temperature by the use of heating elements, thermocouples, insulating tapes, blankets and the like, and by mounting of the reference cell in a thermally controlled chamber, all in a manner well known to those skilled in the art. Still further, the fluid pressure and throughput of the flush liquids in either or both of the two flushing systems may be controlled in a manner well understood by the skilled practitioner, by suitable valving, pumps and computerized operation, either in isolation or in conjunction with electrochemical analyses of quiescent liquids or of chemical processing fluids.

A representative application of the invention is the use of a pH reference electrode, embodying the invention, for monitoring the pH of reactant streams for the production of sodium ethylene bisdithiocarbamate fungicide by the continuous reaction in aqueous medium of carbon disulfide, ethylenediamine and caustic (sodium hydroxide). The pH monitoring is continuously required to control the caustic concentration. A problem in this monitoring is reaction of the sulfide ion, present in the reaction medium as carbon disulfide or product, with the heavy metal salts of a conventional pH reference electrode to form sulfide precipitates at the electrode junction. Over a period of time the precipitates will cause false readings and eventual interruption of pH measurement. When using a reference electrode of the invention, however, periodic flushing of the dual flushing systems of the electrodes effectively prevents collection of precipitate at the junctions, thus forestalling interruption of the pH measurements. Similar benefits are achievable in other chemical process streams where sulfide ion, or other contaminant, may be present.

It will be understood that the foregoing embodiments of the invention are illustrative only, and that various changes can be made in the form, details, spatial arrangements, materials and proportions of the various parts in such embodiments without departing from the spirit and scope of the invention as defined by the appended claims.

I claim:

1. A flushable electrochemical reference cell comprising, in combination:
   a first tubular standard electrolyte-containing compartment having an ion permeable member defining a first junction adapted for contact, exteriorly thereof, with a sample solution;
   a second tubular, standard electrolyte-containing compartment having an ion permeable member defining a second junction adapted for contact, exteriorly thereof, with the standard electrolyte contained in the first tubular compartment;
   a third tubular, standard electrolyte and standard electrode-containing compartment having an ion permeable member defining a third junction adapted for contact, exteriorly thereof, with the standard electrolyte contained in the second tubular compartment, the third tubular compartment including a conductor for electrical contact between the electrode and a potentiometer;
   first fluid conducting means between the interior of the first tubular compartment and the exterior of the second tubular compartment;
   second fluid conducting means between the interior of the second tubular compartment and the exterior of the third tubular compartment;
   a first fluid conduit positioned to deliver a first flushing liquid to the first junction interiorly of the first tubular compartment, and to the second junction exteriorly of the second tubular compartment;
   first exit means for removal of the first flushing liquid;
   a second fluid conduit positioned to deliver a second flushing liquid to the second junction interiorly of the second tubular compartment, and to the third junction exteriorly of the the third tubular compartment; and
   second exit means for removal of the second flushing liquid.

2. The reference cell of claim 1 wherein the first exit means is at a higher elevation than the first and second junctions, and the second exit means is at a higher elevation than the third junction, whereby air which may collect around the junctions will pass out of the cell.

3. The reference cell of claim 1 wherein the flushing liquids contain at least one electrolytic component in common with an electrolytic component of the standard electrolyte in the third tubular compartment.

4. The reference cell of claim 1 wherein the second flushing liquid contains an electrolytic component capable of removing a contaminant or insoluble material which bypasses the second junction and enters the second tubular compartment.

5. The reference cell of claim 1 wherein the point of entry of the first flushing liquid to the first fluid conduit and the first exit means are at higher elevations than the first and second junctions; the point of entry of the second flushing liquid to the second fluid conduit is at a lower elevation than the second and third junctions; and the second exit means is at a higher elevation than the second and third junctions.

6. The reference cell of claim 1 wherein the sample solution comprises a moving stream, and said cell further including fluid pressure equalizing means between the moving stream and the electrolyte in the third tubular compartment.

7. The reference cell of claim 6 wherein the pressure equalizing means comprises a U-shaped tube connecting the third tubular compartment and the moving stream, said U-shaped tube containing at least one electrolytic component in common with an electrolytic component of the standard electrolyte in the third tubular compartment.

8. The reference cell of claim 7 wherein the electrolytic component contained in the U-shaped tube comprises a material capable of removing a contaminant which enters the U-shaped tube from the moving stream.

9. The reference cell of claim 1 wherein the point of entry of the first flushing liquid to the first fluid conduit and the first exit means are at higher elevations than the first and second junctions; the point of entry of the second fluid conduit is at a lower elevation than the second and third junctions; the second exit means is at a higher elevation than the second and third junctions; and wherein the sample solution comprises a moving stream; said cell further including fluid pressure equalizing means between the moving stream and the electrolyte in the third tubular compartment.

* * * * *